United States Patent
Terada et al.

[11] Patent Number: 5,949,847
[45] Date of Patent: Sep. 7, 1999

[54] X-RAY ANALYZING APPARATUS AND X-RAY IRRADIATION ANGLE SETTING METHOD

[75] Inventors: Shinichi Terada; Mikihisa Masaki, both of Hirakata, Japan

[73] Assignee: Technos Institute Co., Ltd., Osaka, Japan

[21] Appl. No.: 08/956,646

[22] Filed: Oct. 23, 1997

[30] Foreign Application Priority Data

Oct. 25, 1996 [JP] Japan ................................. P8-284259
May 7, 1997 [JP] Japan ................................. P9-117228

[51] Int. Cl.[6] ................................................ G01N 23/223
[52] U.S. Cl. ................................................ 378/90; 378/86
[58] Field of Search ................................. 378/44, 45, 46, 378/86, 88, 89, 90, 207

[56] References Cited

U.S. PATENT DOCUMENTS 5,220,591 6/1993 Ohsugi et al. ............................. 378/45
5,457,726 10/1995 Miyazaki ..................................... 378/45

FOREIGN PATENT DOCUMENTS

004244242A1 6/1994 Germany ..................................... 378/46
3-202760 9/1991 Japan .
4-208900 7/1992 Japan .

*Primary Examiner*—David P. Porta
*Attorney, Agent, or Firm*—Wenderoth, Lind & Ponack, L.L.P.

[57] ABSTRACT

An X-ray analyzing apparatus includes an X-ray tube, a monochromator crystal for making an X-ray monochromic, a slit, a moving table for supporting a product to be tested such as a semiconductor wafer, a detector for detecting the intensity of the X-ray beam, a table controller for setting a three-dimensional position and an angle of the moving table, and another detector for detecting scattered X-rays or fluorescent X-rays from the test product. A slit is provided so as to be vertically movable between the test product and the detector and to define a pass position of the X-ray beam which enters the detector. Thus, an X-ray irradiation angle to the test product can be set quickly and at high precision.

5 Claims, 8 Drawing Sheets

X-RAY ANALYZING APPARATUS AND X-RAY IRRADIATION ANGLE SETTING METHOD

BACKGROUND OF THE INVENTION

1. Field of the Invention

The present invention relates to an X-ray analyzing apparatus for irradiating exciting X-rays to a product to be tested such as a semiconductor wafer to analyze fluorescent X-rays generated from the product by EDX (Energy Dispersive X-ray Spectrometry) and to measure surface roughness, thickness of film on the surface, density of the surface and other characteristics of the product by analyzing reflectivity of the X-rays. The present invention also relates to an X-ray irradiation angle setting method for setting an irradiation angle of X-rays to the product.

2. Description of Related Art

Hitherto, there has been known a total reflection X-ray fluorescence analyzing apparatus for irradiating X-rays to a product to be tested such as a semiconductor wafer having an optically flat plane at a low incident angle to detect fluorescent X-rays from a sample adhering on a surface of the product. It allows information only in the vicinity of the surface of the product to be obtained with a high S/N (signal to noise) ratio by totally reflecting the exciting X-rays on the surface of the product.

Further, there has been proposed a monochromic total reflection X-ray fluorescence analyzing apparatus (Japanese Patent Application 1-272124(1989)) for irradiating a characteristic X-ray which is generated from an anode of an X-ray source to a product to be tested after separating X-rays of a single characteristic by spectroscopic apparatuses, e.g., a spectroscopic crystal, a slit and others. Because it allows background noise to be reduced by separating as the monochromic exciting X-rays and the limit for detecting the trace element to be improved, it is rapidly spreading, in particular, in the field for detecting contaminants caused by a trace metal on a semiconductor wafer for LSIs.

Figure 9:
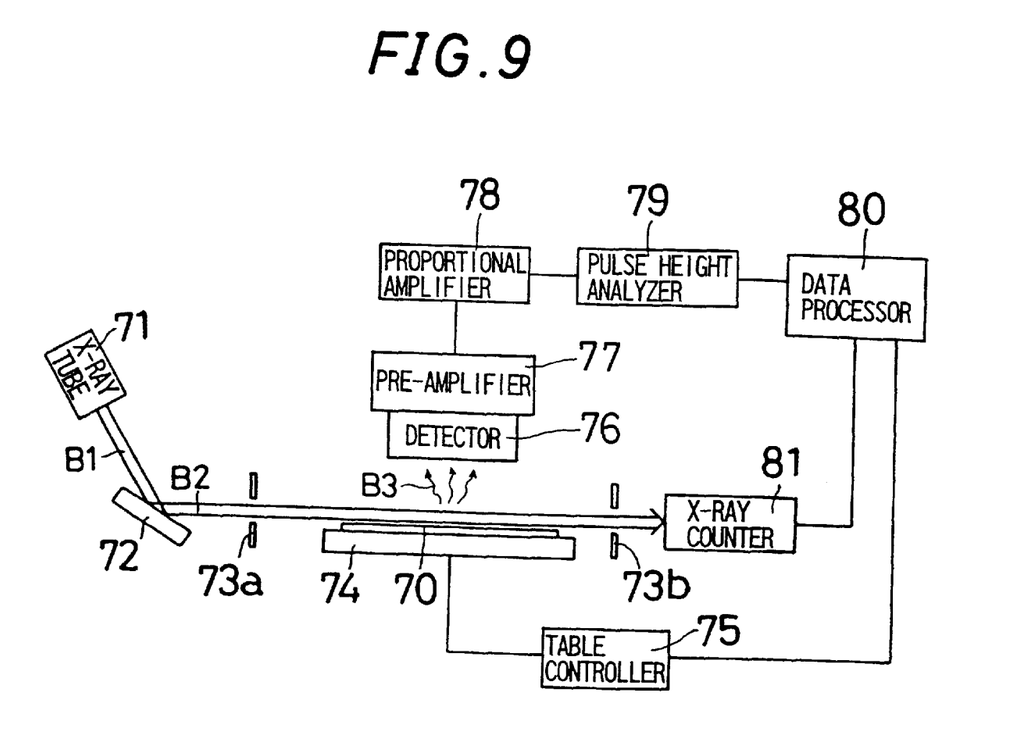
FIG. 9 is a structural diagram showing one example of the conventional X-ray fluorescence analyzing apparatus.

FIG. 9 is a structural diagram showing an example of the conventional X-ray fluorescence analyzing apparatus. This X-ray fluorescence analyzing apparatus comprises an X-ray tube 71 for generating an X-ray beam B1, a monochromator crystal 72 for separating an X-ray beam B2 composed of a single characteristic X-ray from the X-ray beam B1, a collimator 73a for blocking other characteristic X-rays, a moving table 74 for supporting a product to be tested 70 (hereinafter referred to as "test product") such as a semiconductor wafer, a collimator 73b for blocking scattered X-rays other than the X-ray beam B2, an X-ray counter 81 for measuring the intensity of the X-ray beam B2, a table controller 75 for setting three-dimensional position of the moving table 74 and an angle thereof to the X-ray beam B2, a detector 76 for detecting fluorescent X-rays B3 generated from the test product 70, a pre-amplifier 77 for converting into stepped voltage pulses having a pulse height of the time integral value of the charge pulse outputted from the detector 76, a proportional amplifier 78 for shaping the waveform as a pulse having a pulse height proportional to a width of a leading edge of a voltage pulse outputted from the pre-amplifier 77, a pulse-height analyzer 79 for measuring a counting rate of each peak value outputted from the proportional amplifier 78, a data processor 80 for processing data measured by the wave-height analyzer 79 and the X-ray counter 81 and for issuing commands to the table controller 75, and others. Information about the vicinity of a surface of the test product 70, e.g. information on concentration of trace contaminants, can be obtained by irradiating the X-ray beam B2 to enter the surface of the test product 70 at an angle to the surface where the beam totally reflects, e.g. an angle of about 0.06 degrees.

A method for setting an angle for irradiating the energy beam to the test product 70 in the X-ray fluorescence analyzing apparatus shown in FIG. 9 has been proposed in Japanese Patent Application No. 2-400231 and others.

Figures 10A, 10B:
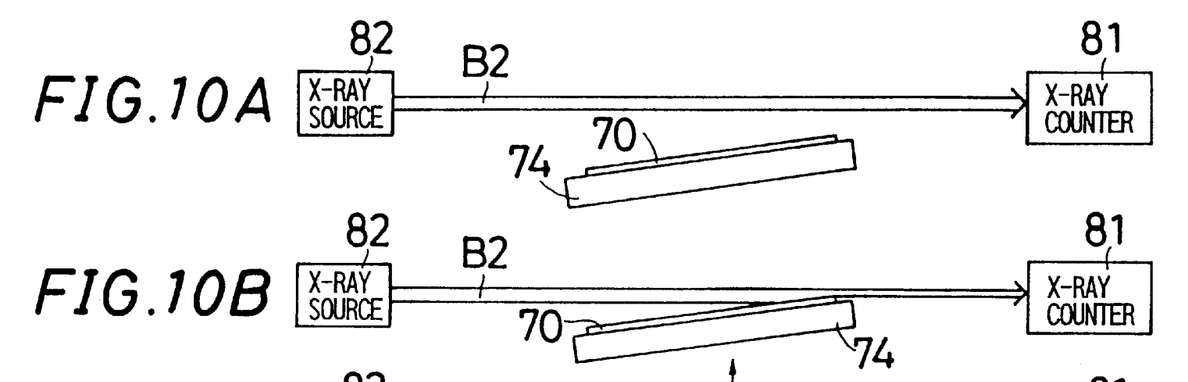
FIGS. 10A through 10E are process diagrams showing an X-ray irradiation angle setting method in the apparatus in FIG. 9.

FIGS. 10A through 10E are flow diagrams showing a method for setting an irradiation angle in the apparatus of FIG. 9. At first, as shown in FIG. 10A, the X-ray beam B2 outputted from an X-ray source 82 composed of either the X-ray tube 71, or the X-ray tube 71 and the monochromator crystal 72, is caused to directly enter the X-ray counter 81 to measure the intensity of the X-ray beam B2 to store the initial value of intensity in a memory or the like within the data processor 80. At this time, the test product 70 is set at a position where the test product will not block the X-ray beam B2, to be inclined slightly with respect to the X-ray source 82.

Next, as shown in FIG. 10B, the table controller 75 drives the moving table 74 to raise the test product 70 gradually, while the intensity of X-ray is measured by the X-ray counter 81. When the test product 70 gradually blocks the X-ray beam B2 and the intensity of the X-rays outputted by the X-ray counter 81 reaches a reference value, e.g. a half of the initial value of intensity, the test product 70 is stopped from rising.

Figure 10C:
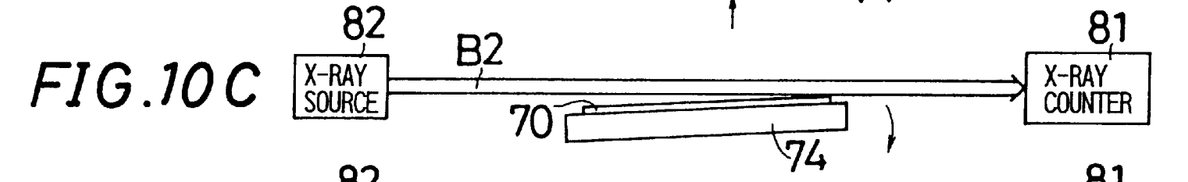

Then, as shown in FIG. 10C, while on the basis of a command from the data processor 80, the inclination angle of the test product 70 is changed so that the inclination approaches the horizontal direction, the intensity of the X-ray beam is measured by the X-ray counter 81, and when the intensity outputted by the X-ray counter 81 reaches a relative maximum, the angular displacement of the test product 70 is stopped. When the relative maximum value of the intensity of the X-ray beam at this time is greater than the reference value, it is determined that the test product 70 is not parallel with the X-ray beam B2 and the test product 70 is gradually raised in FIG. 10D similarly to FIG. 10B to control the test product 70 in vertical position so that the intensity of the X-ray beam coincides with the reference value.

Figures 10D, 10E:
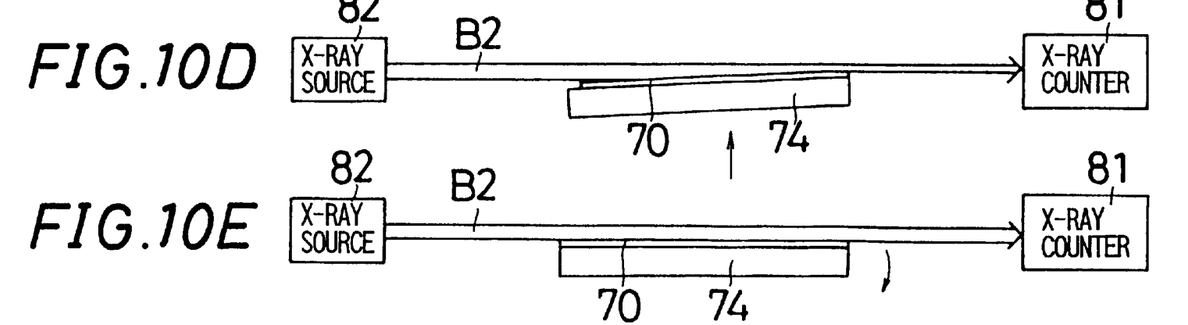

Next, as shown in FIG. 10E, the same as in FIG. 10C, the test product 70 is controlled to be gradually angularly displaced so that the intensity of the X-ray beam reaches the relative maximum value.

Raising and angularly displacing the test product 70 is thus repeated, and when the reference value brought about by the raising operation becomes equal to the relative maximum value brought about by the angular displacement, the traveling direction of the X-ray beam B2 is set parallel with the surface of the test product 70. After that, the table controller 75 drives the moving table 74 so that the X-ray beam B2 is irradiated at an incident angle of a predetermined total reflection angle. The setting of the irradiation angle of the X-ray beam B2 to the test product 70 is thus completed.

Because the exciting X-ray beam itself is thus used for the adjustment and the position and the angle can be adjusted accurately, the elapsed fluctuation error of the X-ray beam axis can be absorbed by the adjustment even if it occurs. Further, even if the peripheral edge of the test product 70 is curved and drops by its own weight, the part around the center from which the fluorescent X-rays are generated is correctly adjusted. Further, it allows a desirable incident angle to be set to the upper most face of a semiconductor wafer when a semiconductor wafer on which patterns have been formed is measured as a test product.

Meanwhile, beside the measurement using such fluorescent X-rays, there has been developed a method for measuring surface information, e.g. surface roughness, thickness of thin film, density and others, of a test product by irradiating X-rays at a very low angle and by directly measuring the intensity of X-rays reflected by the test face.

The measurement of surface roughness utilizes the nature that the rougher the surface of the test product, the lower the X-ray reflectivity is, and the incident angle of X-ray must be accurately set.

The measurement of thickness of thin film utilizes an interference caused by a difference of optical paths of X-rays reflected by the surface of the film and X-rays which pass through the film and are reflected by the surface of a test product, to measure a period of reflectivity of X-rays which changes according to the incident angle of the X-rays. The incident angle of the X-rays must be set at high precision also in this measurement.

The measurement of density specifies the density of the surface of a test product by measuring a critical incident angle on the surface of the test product and the X-ray incident angle must be set at high precision also in this measurement.

The apparatus is arranged such that an X-ray detector is disposed in the direction in which the X-rays are reflected in such measurement of reflectivity of X-rays, and the apparatus shown in FIG. 9 may be also used.

However, the apparatus shown in FIG. 9 has a problem that because the intensity of X-rays is measured by using the X-ray counter 81 while alternately controlling the height and angle of the moving table 74, it takes time for the measurement.

Further, when the face of the test product 70 is not an ideal plane and is deformed by warp or distortion, the X-ray irradiation angle at the actual irradiation point deviates from the setting angle of the moving table 74, containing a deformation error. The dependency on angle of the X-ray reflectivity is an important measurement item in the measurement of surface roughness, thickness, density and others of the test product 70, and the measured result is largely swayed if there is even a slight error in the X-ray irradiation angle.

SUMMARY OF THE INVENTION

It is hence an object of the present invention to provide an X-ray analyzing apparatus and an X-ray irradiation angle setting method, capable of quickly and precisely setting the X-ray irradiation angle to a test product.

The invention provides an X-ray analyzing apparatus comprising:

beam irradiating device operable to irradiate an X-ray beam to a test face of a product to be tested at a predetermined angle;

a first X-ray detector operable to detect an intensity of the X-ray beam reflected by the test face;

a slit provided between the product and the first X-ray detecting means, for defining a pass position of the X-ray beam which enters the first X-ray detector;

a slit controller operable to control position of the slit;

product supporting device operable to support the product to control a three-dimensional position of the test face and an angle of the test face to the X-ray beam; and a second X-ray detector provided almost right above an inspection point, for detecting an intensity of scattered X-rays or fluorescent X-rays from the test face.

The present invention utilizes the principle that by specifying the position and direction of an incident X-ray beam and the irradiation position on the test product, the axis of a reflected X-ray beam is uniquely determined when an irradiation angle is set to a predetermined one. Accordingly, the desirable X-ray irradiation angle can be set by accurately positioning the slit at the position where the reflected X-ray beam should pass through and by controlling the three-dimensional position and angle of the test face so that the intensity of the X-rays which pass through the slit is maximized. Because the reflection condition at the X-ray irradiation position on the test face can be correctly set even if the test product has a deformation such as a warp, a deformation error of the test product can be eliminated.

Further, the X-ray irradiation position of the test product can be accurately set by monitoring a signal from the second X-ray detector provided almost right above the inspection point.

The invention provides an X-ray analyzing apparatus comprising:

X-ray beam irradiating device operable to irradiate an X-ray beam to a test face of a product to be tested at a predetermined angle;

a first X-ray detector operable to detect positions and intensity distributions of the X-ray beam which has straightly passed through above the test face and of the X-ray beam which has been reflected by the test face;

a product supporting means device operable to support the product to control a three-dimensional position of the test face and incident and torsion angles of the test face to the X-ray beam; and a second X-ray detector provided almost right above an inspection point, operable to detect an intensity of scattered X-rays or fluorescent X-rays from the test face.

According to the invention, the incident angle of the test face to the X-ray beam can be specified by detecting pass positions of the straight-ahead X-ray beam and reflected X-ray beam. Further, the torsion angle of the test face to the X-ray beam can be specified by detecting intensity distributions of the straight-ahead X-ray beam and reflected X-ray beam and by comparing them to each other. It is noted that the torsion angle is defined by an inclination angle around the Y-axis of the test face in an orthogonal coordinate system when the test face is slightly inclined around the Y-axis and the reflected X-ray beam is deviated from a YZ plane when the incident X-ray beam and reflected X-ray beam travel within the YZ plane with respect to the test face set in parallel with a XY plane.

The desirable X-ray irradiation angle can be set by adjusting the three-dimensional position and angle of the test face so that the incident angle of the test face turns out to be a desirable value and the torsion angle of the test face is zeroed. Because the reflection condition at the X-ray irradiation position on the test face can be correctly set even if the test product has a deformation such as a warp at this time, a deformation error of the test product can be eliminated.

Further, the X-ray irradiation position of the test product can be accurately set by monitoring a signal from the second X-ray detector provided almost right above the inspection point.

The invention provides an X-ray analyzing apparatus comprising:

an X-ray beam irradiating device operable to irradiate an X-ray beam to a test face of a product to be tested at a predetermined angle;

a slit in which a first opening for defining a pass position of the X-ray beam which has straightly passed through above the test face and a second opening for defining a pass position of the X-ray beam reflected by the test face are formed;

a first X-ray detector operable to detect an intensity of the X-ray beam which has passed through the first or second opening;

product supporting device operable to support the product to control a three-dimensional position of the test face and an angle of the test face to the X-ray beam; and a second X-ray detector provided almost right above an inspection point, operable to detect an intensity of scattered X-rays or fluorescent X-rays from the test face.

According to the invention, it is possible to quickly determine whether the X-ray beam enters the test face at an adequate angle and an adequate position by setting in advance the positions of the first and second openings of the slit and a distance from the inspection point to the slit so that they conform to a desired X-ray irradiation condition, by confirming that the straight-ahead X-ray beam passes through the first opening based on the signal detected by the first X-ray detector and by confirming that the reflected X-ray beam passes through the second opening in adjusting the position and angle of the test face.

Because the X-ray irradiation condition of the test face can be correctly set even if the test product has a deformation such as a warp at this time by monitoring the intensities of X-ray beams which have passed through the first and second openings, the adjusting works for eliminating the deformation error of the test product can be conducted simply.

Further, the X-ray irradiation position of the test product can be accurately set by monitoring a signal from the second X-ray detector provided almost right above the inspection point.

Further, the invention provides an X-ray irradiation angle setting method for setting an irradiation angle of an X-ray beam to a test face of a product to be tested comprising;

disposing a slit for defining a pass position of the X-ray beam reflected by the test face to set height H of the slit to L×tan 2φ, wherein L is a horizontal distance from the inspection point to the slit and φ is an irradiation angle at the time of measurement, and adjusting an angle of the product within a reflection plane so that the X-ray beam reflected by the test face passes through the slit.

According to the invention, the desirable X-ray irradiation angle can be set by specifying an optical axis of the reflected X-ray beam based on the horizontal distance L from the inspection point to the slit and the irradiation angle φ at the time of measurement, and by adjusting the angle of the test product within the reflection plane so that the X-ray beam reflected by the test face passes through the slit after setting the height H of the slit so as to coincide with the optical axis. It is noted that when the irradiation angle φ is small, it can be approximated by tan 2φ≈2φ.

In this case, the reflection condition at the X-ray irradiation position on the test face can be correctly set and the deformation error can be eliminated even if the test product has a deformation such as a warp.

The invention provides an X-ray irradiation angle setting method for setting an irradiation angle of an X-ray beam to a test face of a product to be tested comprising;

setting a height of the product by detecting a change in intensity of the X-ray beam blocked by the product while moving the product in a direction almost perpendicular to the traveling direction of the X-ray beam;

adjusting an angle of the product to the incident X-ray beam within a reflection plane to be set at a predetermined irradiation angle;

disposing a slit for defining a pass position of the X-ray beam reflected by the test face and setting height H of the slit to L×tan 2φ, where L is a horizontal distance from the inspection point to the slit and φ is an irradiation angle at the time of measurement, disposing a X-ray detector for detecting scattered X-rays or fluorescent X-rays from the test face almost right above the inspection point to adjust the height of the test product so that a signal from the X-ray detector is maximized; and adjusting an angle of the product within the reflection plane so that the X-ray beam reflected by the test face passes through the slit.

According to the invention, the height of the test product can be set by detecting the change in intensity of the X-ray beam blocked by the test product while moving the test product in the direction almost perpendicular to the traveling direction of the X-ray beam and the X-ray irradiation angle can be set by controlling the angle of the test product. When the test face of the test product is an ideal plane in this stage, the setting of the irradiation angle is finished.

On the other hand, when the test product is warped, both the X-ray irradiation angle and the irradiation position deviate from the desirable measuring conditions. In order to deal with that, an optical axis of the reflected X-ray beam is specified on the basis of the horizontal distance L from the inspection point to the slit and the irradiation angle φ at the time of measurement and the height H of the slit is set so as to coincide with the optical axis. Then, the irradiation position can be made coincident with the inspection point by adjusting the height of the test product while monitoring a signal from the X-ray detector disposed almost right above the inspection point and by moving the irradiation position on the test product forward or backward. Next, the desirable X-ray irradiation angle can be set by controlling the angle of the test product within the reflection plane so that the X-ray beam reflected by the test face passes through the slit. It is noted that when the irradiation angle φ is small, it can be approximated by tan 2φ≈2φ.

When the shift of the X-ray irradiation position is left by making such an adjustment, it is converged by repeatedly adjusting the height and angle of the test product by several times.

The reflection condition at the X-ray irradiation position on the test face can be correctly set and the deformation error can be eliminated even if the test product has a deformation such as a warp.

The invention provides an X-ray irradiation angle setting method for setting an irradiation angle of an X-ray beam to a test face of a product to be tested, comprising;

detecting an intensity distribution and a position of the X-ray beam which straightly passed through above the test face;

adjusting an angle of the product to the incident X-ray beam within a reflection plane to set at a predetermined incident angle;

detecting an intensity distribution and a position of the X-ray beam reflected by the test face; and adjusting a torsion angle of the product to the incident X-ray beam so that the intensity distribution of the reflected X-ray beam coincides with the intensity distribution of the straight-ahead X-ray beam.

According to the invention, the incident angle of the test face to the X-ray beam can be specified by detecting the pass positions of the straight-ahead X-ray beam and reflected X-ray beam. Further, the torsion angle of the test face to the X-ray beam can be specified by detecting intensity distributions of the straight-ahead X-ray beam and reflected X-ray beam and by comparing them to each other.

The desirable X-ray irradiation angle can be set by adjusting the three-dimensional position and the angle of the test face so that the incident angle of the test face turns out to be a desirable value and the torsion angle of the test face is zeroed. Because the reflection condition at the X-ray irradiation position on the test face can be correctly set even if the test product has a deformation such as a warp at this time, a deformation error of the test product can be eliminated.

Further, the X-ray irradiation position of the test product can be accurately set by monitoring a signal from the second X-ray detector provided almost right above the inspection point.

The invention provides an X-ray irradiation angle setting method for setting an irradiation angle of X-ray beam to a test face of a product to be tested, comprising;

disposing a slit in which a first opening for defining a pass position of the X-ray beam which has straightly passed through above the test face and a second opening for defining a pass position of the X-ray beam reflected by the test face and setting height H of the second opening to L×tan 2$\phi$, where L is a horizontal distance from the inspection point to the slit and $\phi$ is an irradiation angle at the time of measurement; and adjusting an incident angle of the product within the reflection plane so that the X-ray beam reflected by the test face passes through the second opening.

According to the invention, it is possible to quickly determine whether the X-ray beam enters the test face with an adequate angle and an adequate position by setting in advance the positions of the first and second openings of the slit s and a distance from the inspection point to the slit so that they conform to a desired X-ray irradiation condition H=L×tan 2$\phi$, and upon confirming that the straight-ahead X-ray beam passes through the first opening, by adjusting the position and angle of the test face so that the reflected X-ray beam passes through the second opening. It is noted that when the irradiation angle $\phi$ is small, it can be approximated by tan 2$\phi \approx$ 2$\phi$.

The reflection condition at the X-ray irradiation position on the test face can be correctly set and the deformation error can be eliminated even if the test product has a deformation such as a warp.

BRIEF DESCRIPTION OF THE DRAWINGS

Other and further objects, features, and advantages of the invention will be more explicit from the following detailed description taken with reference to the drawings wherein.

DETAILED DESCRIPTION OF THE PREFERRED EMBODIMENTS

Now referring to the drawings, preferred embodiments of the invention are described below.

Figure 1:
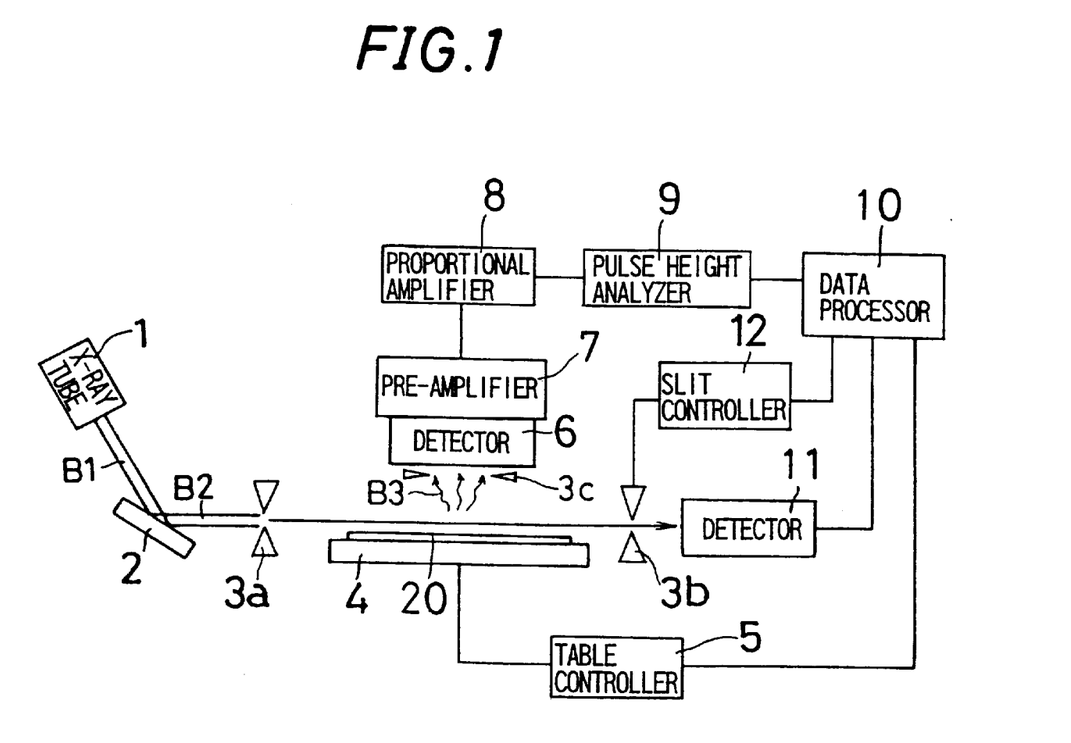
FIG. 1 is a structural diagram showing a first embodiment of the invention.

FIG. 1 is a structural diagram showing a first embodiment of the invention. An X-ray analyzing apparatus comprises an X-ray tube 1 for generating an X-ray beam B1, a monochromator crystal 2 for separating an X-ray beam B2 composed of a single characteristic X-ray from the X-ray beam B1, a slit 3a for blocking other characteristic X-rays, a moving table 4 for supporting a test product 20 such as a semiconductor wafer, a detector 11 for detecting the intensity of the X-ray beam B2, a table controller 5 for setting a three-dimensional position and an angle of the moving table 4 with respect to the X-ray beam B2, a detector 6 for detecting a fluorescent X-ray B3 generated from the test product 20, and others. The detector 6 is provided with an aperture 3c for defining a light receiving angle.

Further, a slit 3b is provided between the test product 20 and the detector 11 to define a pass position of the X-ray beam B2 which enters the detector 11. The slit 3b is allowed to move up and down and its position is controlled by a slit controller 12 based on a command from a data processor 10. It is also possible to arrange the slit 3b so as to move circularly on a circle centering on an inspection point.

With respect to a signal processing system, there are provided a pre-amplifier 7 for amplifying a signal from the detector 6, a proportional amplifier 8 for shaping waveforms as a pulse having a pulse height proportional to a width of a leading edge of a charge pulse outputted from the pre-amplifier 7, a pulse-height analyzer 9 for measuring a counting rate of each peak value outputted from the proportional amplifier 8, a data processor 10 for processing data measured by the pulse-height analyzer 9 and the detector 11, and issuing commands to the table controller 5 and others.

Herein is shown an example of the structure which is used for the total reflection X-ray fluorescence analysis and the X-ray reflectivity measurement and a semiconductor detector is used as the detector 6. In a structure for conducting only the X-ray reflectivity measurement, a scintillation counter, a proportional counter, an ion chamber, a GM counter and a semiconductor detector may be used as the detector 6 and the aforementioned signal processing system for energy analysis is not necessary.

The detector 11 is used for measuring the intensity of primary X-rays and reflected X-rays, which may be a scintillation counter, a proportional counter, an ion chamber, a GM counter or a semiconductor detector. The slit 3b may be replaced by a collimator built in the detector 11 in advance. The position of the whole detector 11 is controlled by the slit controller 12 in such a case.

The X-ray tube 1 may be a fixed anode type or a rotating anode type tube. The monochromator crystal 2 may be a single crystal or may be a combination of two or more crystals. It may be omitted when no monochromic X-ray is necessary in the content of analysis.

The X-ray beam B2 enters the surface of the test product 20 at an angle where the X-ray beam totally reflects, e.g. at an angle of about 0.06 degrees. Information about the vicinity of the surface of the test product 20, e.g. information on concentration of trace contaminants, can be obtained by analyzing energy spectrum of the fluorescent X-rays B3 at this time. Further, the surface roughness, thickness of thin film, density and others of the test product 20 can be defined by measuring the reflectivity of the X-rays on the test product 20 from the intensity signal from the detector 11.

FIGS. 2A through 2D are process diagrams showing an X-ray irradiation angle setting method according to a first embodiment. At first, the test product 20 is set on the moving table 4 shown in FIG. 1 and the height of the moving table 4 is controlled so that the X-ray beam B2 will not impinge on the test product 20. Here, a case in which the X-ray beam B2 travels in the horizontal direction (dashed line in FIG. 2) is shown. Next, the height of the slit 3b is controlled so that the signal of the detector 11 is maximized. This position is defined as a reference height H0.

Figure 2A:
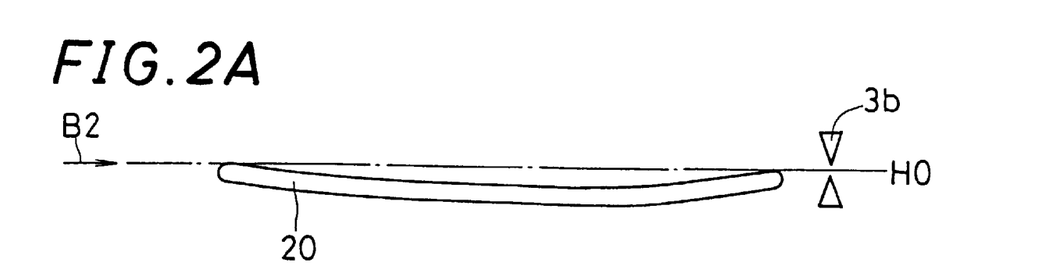
FIGS. 2A through 2D are process diagrams showing an X-ray irradiation angle setting method according to the invention.

Next, the three-dimensional position and angle of the test product 20 and the moving table 4 are controlled by detecting the change in intensity of the X-ray beam which is blocked by the test product 20 similarly to the procedure shown in FIG. 10 such that the traveling direction of the X-ray beam B2 becomes parallel with the face of the test product 20 as shown in FIG. 10E. Next, the change in intensity of the X-ray beam B2 which is blocked by the test product 20 is detected while moving the test product 20 in the direction almost perpendicular to the traveling direction of the X-ray beam B2 to set the test product 20 at height just before it contacts with the X-ray beam B2 as shown in FIG. 2A. It is noted that FIGS. 2A through 2D show a case when the test product 20 has a concaved deformation.

Figures 2B, 2C:
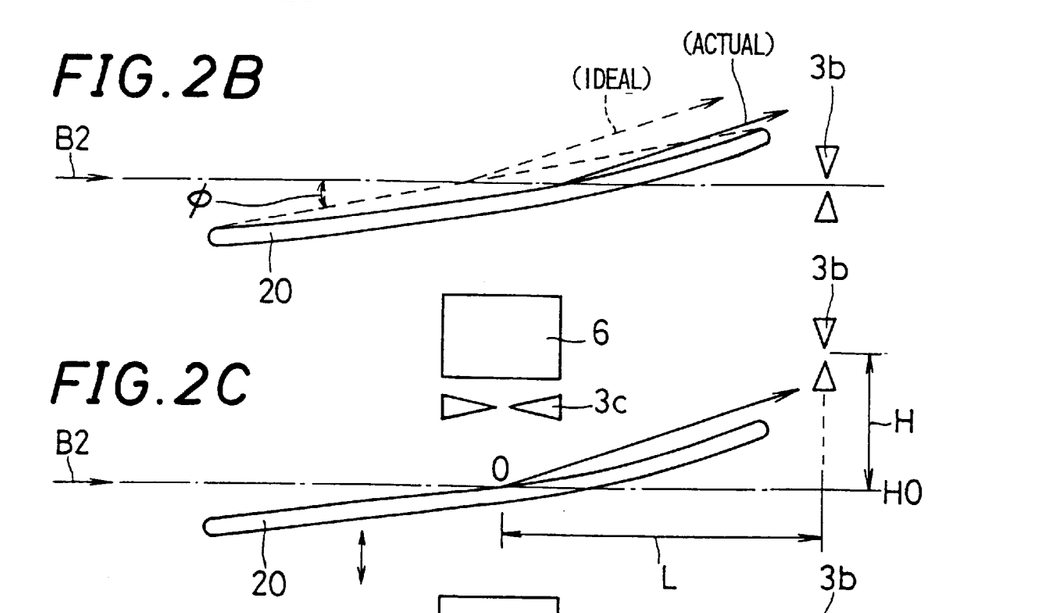

Next, the moving table 4 is inclined to set the incident angle to the X-ray beam B2 at a desirable angle $\phi$ as shown in FIG. 2B. This angle $\phi$ is a fully large angle which causes no blocked part due to the deformation, seeing the face of the test product 20 from the X-ray incident direction, and a very low angle which allows a full intensity of reflected X-rays to be maintained. It is preferable to be within a range of 0.05 to 0.3 degrees when the test product 20 is a silicon wafer for example.

If the face of the test product 20 is an ideal plane (indicated by a broken line in the FIG. 2B) in this state, the setting of the X-ray irradiation angle is finished. However, because the test product 20 has a deformation such as a warp more or less in general, the position where the X-ray beam B2 impinges on the test face is displaced in the horizontal direction and the X-ray incident angle is also shifted from the angle $\phi$.

In order to deal with that, the slit 3b for defining the pass position of the X-ray beam B2 reflected by the test face is moved above to set the height H of the slit 3b at L×tan 2$\phi$, where L is a horizontal distance from the inspection point to the slit 3b and $\phi$ is an irradiation angle at the time of measurement. The position of the slit 3b is a position where a regular reflection axis passes through when the X-ray incident angle is the angle $\phi$. It is noted that when the irradiation angle $\phi$ is small, it can be approximated by tan 2$\phi \approx$ 2$\phi$.

Next, in order to make the irradiation position of the X-ray beam B2 coincident with the inspection point O, the detector 6 which is set almost right above the inspection point O detects scattered X-rays or fluorescent X-rays, other than the regular reflection, to control the height of the test product 20 so that the detected intensity is maximized. In this state, the X-ray irradiation position on the test face coincides with the inspection point O set on the light receiving center axis of the detector 6 as shown in FIG. 2C. The movement at this time is set as $\Delta z$.

Figure 2D:
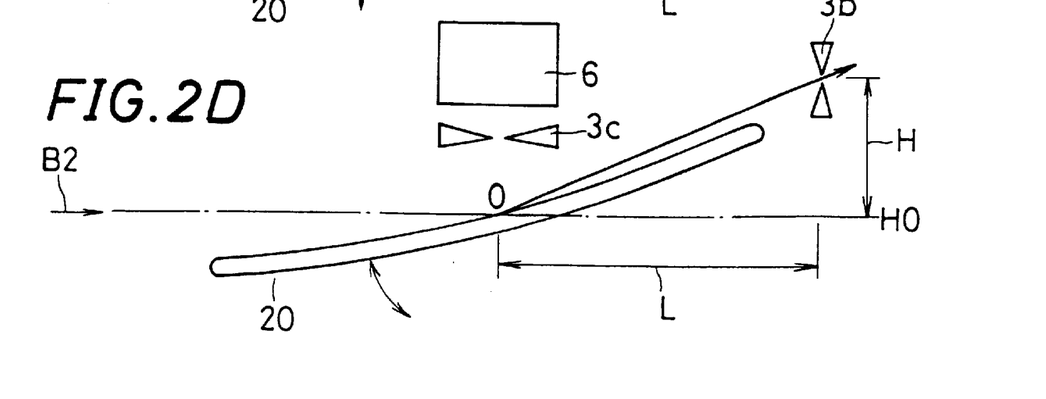

Because the X-ray incident angle is shifted from the angle $\phi$ due to the deformation of the test product 20 in the state shown in FIG. 2C, the axis of reflected X-rays can not pass through the slit 3b. Then, the test product 20 is angularly displaced centering on the inspection point O so that the reflected X-rays pass through the slit 3b as shown in FIG. 2D and the angle of the test face is controlled so that the detected intensity at the detector 11 provided at the back of the slit 3b is maximized. An angular displacement at this time is set as $\Delta \omega$.

Here, because the X-ray irradiation position may be shifted due to the angular control of the test product 20 when the deformation of the test product 20 is large, the height control using the detector 6 and the angular control using the detector 11 are repeated again several times so that the movement $\Delta z$ and the angular displacement $\Delta \omega$ converge below the specified values. It is noted that it is desirable to make the height and the angle of the test product 20 to be set initially closer to the converged values as much as possible in order to converge such controls in a short time and a measuring system using light may be provided separately.

Thus, the X-ray incident angle can be set at high precision and quickly even for the test product having the warp by controlling the three-dimensional position and the angle of the test product such that the detected intensities from the two detectors 6 and 11 are maximized.

Figure 3:
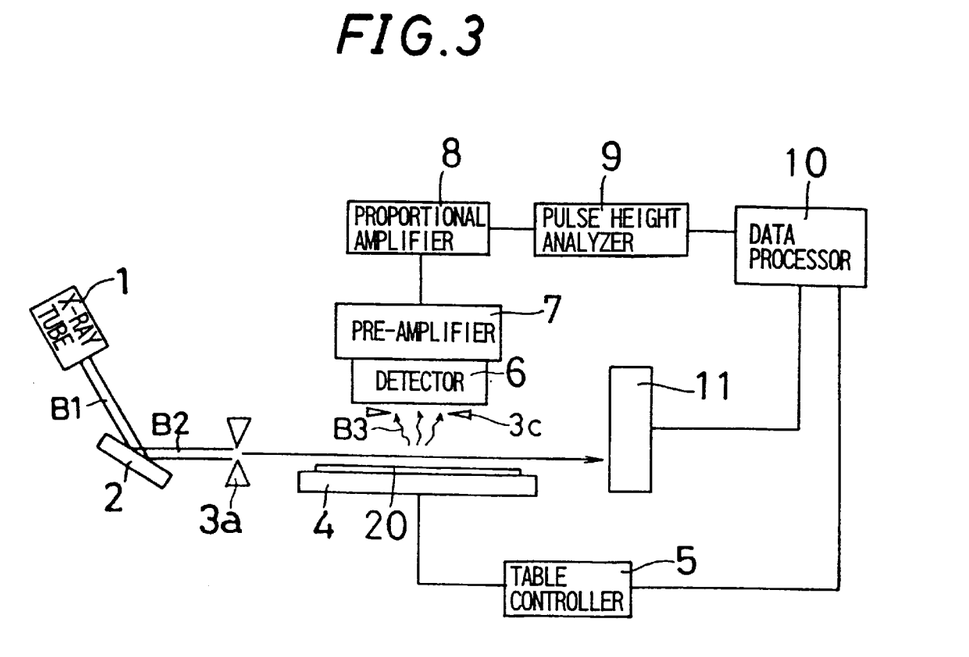
FIG. 3 is a structural diagram showing a second embodiment of the invention.

FIG. 3 is a structural diagram showing a second embodiment of the invention. While the X-ray analyzing apparatus shown in FIG. 3 has the same structure as that shown in FIG. 1, it is different in that the slit 3b and the slit controller 12 are omitted and the detector 11 is composed of a one-dimensional sensor or a two-dimensional sensor which can detect the intensity distribution and pass position of the X-rays. The moving table 4 is arranged so as to be able to control the three-dimensional position of the face of the test product 20, and the incident angle and torsion angle of the X-ray beam B2. It is noted that an explanation thereof which overlaps with that of the first embodiment will be omitted here in order to facilitate the understanding thereof.

Figure 4:
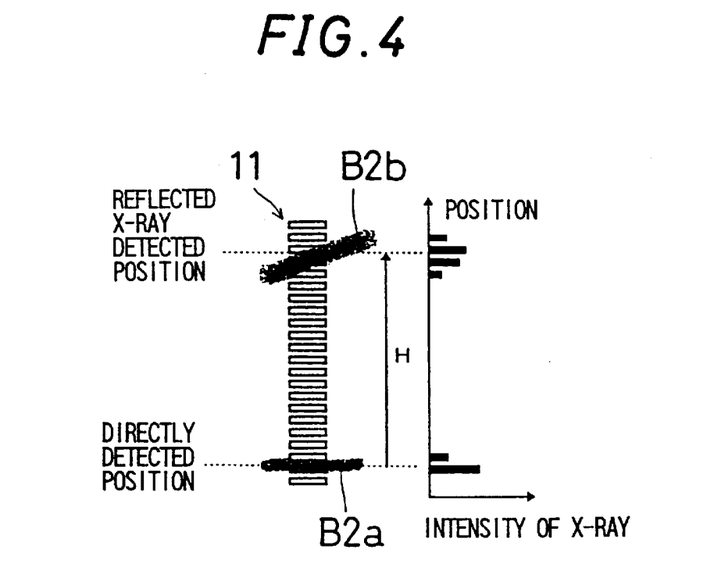
FIG. 4 is an explanatory chart showing pass positions and an intensity distribution of X-ray beam B2 when a one-dimensional sensor is used as a detector 11.

FIG. 4 is an explanatory chart showing the pass positions and intensity distribution of the X-ray beam B2 in the case where the one-dimensional sensor is used as the detector 11. For the detector 11, a one-dimensional sensor in which a plurality of light receiving elements are arranged linearly at a predetermined pitch, e.g. a CCD sensor, or a one-dimensional sensor which generates a light receiving position signal per X-ray photon received, e.g. a position sensitive proportional counter, may be used.

The detector 11 is set so that the position detecting direction thereof is vertical. When the X-ray beam B2 passes through above the test product 20 as it is, it reaches directly at a lower part of the detector 11 and is detected as a direct beam B2a. Because the X-ray beam B2 is shaped into a horizontal slit shape by the slit 3a, the direct beam B2a is detected by the detector 11 as a sharp peak image. The data processor 10 analyzes the signal detected by the detector 11 and detects a peak position of the intensity distribution and an average position of the whole as a center position of the direct beam B2a.

When the position and angle of the test product 20 are controlled so that the X-ray beam B2 is reflected by the test face on the other hand, the beam reaches the upper part of the detector 11 and is detected as a reflected beam B2b. When the longitudinal direction of the X-ray beam B2 is parallel with the test face, i.e. when an torsion angle is zero, the longitudinal direction of the reflected beam 2b is also kept horizontal. However, when a certain torsion angle exists due to the warp or deformation of the test product 20, the longitudinal direction of the reflected beam B2b is inclined by twice of the torsion angle. The data processor 10 analyzes the signal detected by the detector 11 to detect a peak position of the intensity distribution and an average position of the whole as a center position of the reflected beam B2b and detects an extent of the intensity distribution due to the inclination of the reflected beam B2b as a full width at half maximum (FWHM) for example to relate the FWHM with the torsion angle of the reflected beam B2b.

Next, the desirable X-ray irradiation angle can be set by controlling the position and angle of the test product 20 so that the height H from the center position of the direct beam B2a to the center position of the reflected beam B2b, the horizontal distance L from the inspection point to the detector 11 and the incident angle $\phi$ of the X-ray beam B2 satisfy a relational equation H=L×tan 2$\phi$. It is noted that when the angle $\phi$ is small, it can be approximated by tan 2$\phi \approx$ 2$\phi$.

Further, with respect to the torsion angle of the test face, the position and angle of the test product 20 are controlled so that the intensity distribution of the detected signal of the reflected beam B2b becomes sharpest and the full width at half maximum is minimized.

Next, in order to make the irradiation position of the X-ray beam B2 coincident with the inspection point, the detector 6 provided almost right above the inspection point detects scattered X-rays or fluorescent X-rays, other than the regular reflection, to control the height of the test product 20 so that the detected intensity is maximized.

Thus, the conditions related to the incident angle $\phi$ and the torsion angle of the X-ray beam B2 are both met and it is possible to converge to the desirable X-ray irradiation condition by repeatedly controlling the position and angle of the test product 20 so that the irradiation position of the X-ray beam B2 coincides with the desirable inspection point.

Figure 5:
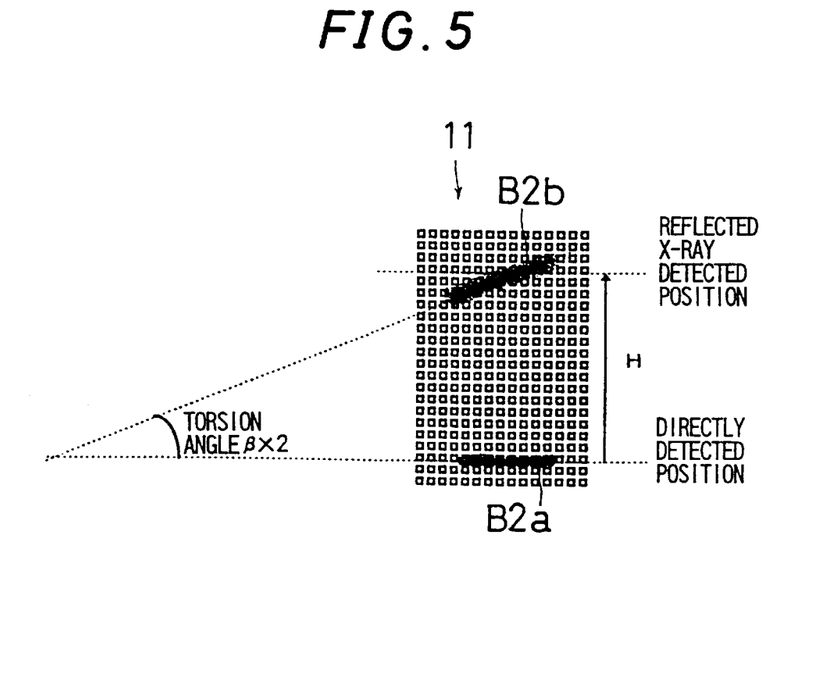
FIG. 5 is an explanatory chart showing pass positions of the X-ray beam B2 when a two-dimensional sensor is used as the detector 11.

FIG. 5 is an explanatory chart showing positions where the X-ray beam B2 passes through when the two-dimensional sensor is used as the detector 11. For the detector 11, a two-dimensional sensor in which a plurality of light receiving elements are arranged in a matrix form at a predetermined pitch, e.g. a CCD sensor, or a two-dimensional sensor which generates a light receiving position signal per X-ray photon received, e.g. a position sensitive proportional counter, may be used.

The detector 11 is set so that the position detecting directions thereof are horizontal and vertical. When the X-ray beam B2 passes through above the test product 20 as it is, it reaches directly at the lower part of the detector 11 and is detected as a direct beam B2a. The data processor 10 analyzes the signal detected by the detector 11 and detects a peak position of the intensity distribution and an average position of the whole as a center position of the direct beam B2a similarly to the explanation made with reference to FIG. 4.

When the X-ray beam B2 is reflected by the test face on the other hand, the beam reaches the upper part of the detector 11 and is detected as a reflected beam B2b. When a certain torsion angle exists due to the warp or deformation of the test product 20, the longitudinal direction of the reflected beam B2b is inclined. The data processor 10 two-dimensionally analyzes the signal detected by the detector 11. It then detects a peak position of the intensity distribution or an average position of the whole as a center position of the reflected beam B2b and relates the angle of inclination of the intensity distribution of the reflected beam B2b with the torsion angle. Because the angle of inclination of the distribution of intensities represented as twice of the torsion angle $\beta$ here, the torsion angle of the test product 20 may be corrected by the half of the angle of inclination inversely.

Next, similarly to the explanation in FIG. 4, it is possible to converge to the desirable X-ray irradiation condition by repeatedly controlling the position and angle of the test product 20 so that the condition of H=L×tan 2$\phi$ is satisfied and so that the angle of inclination of the intensity distribution of the reflected beam B2b is zeroed and so that the irradiation position of the X-ray beam B2 coincides with the desirable inspection point.

Figure 6:
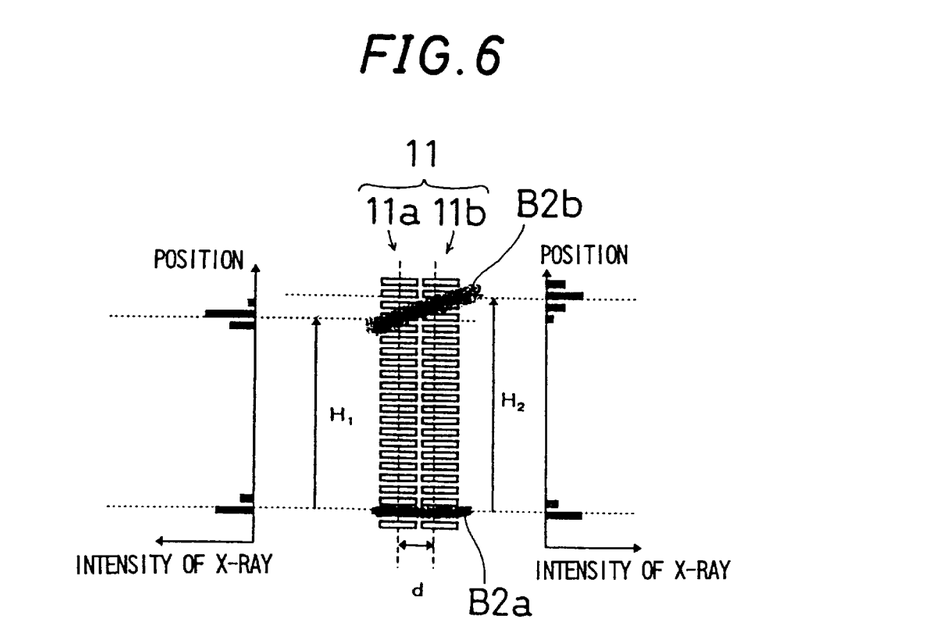
FIG. 6 is an explanatory chart showing pass positions and an intensity distribution of the X-ray beam B2 when two one-dimensional sensors are used as the detector 11.

FIG. 6 is an explanatory chart showing pass positions and intensity distributions of the X-ray beam B2 when two one-dimensional sensors are used as the detector 11. The detector 11 is composed of one-dimensional sensors 11a and 11b in which a plurality of light receiving elements are arranged linearly at a predetermined pitch, respectively. The two one-dimensional sensors 11a and 11b are disposed in parallel with a gap d. For the detector 11, a CCD sensor or a position sensitive proportional counter may be used.

The detector 11 is set so that the position detecting direction thereof is vertical. When the X-ray beam B2 passes through above the test product 20 as it is, it reaches directly at the lower part of the one-dimensional sensors 11a and 11b and is detected as a direct beam B2a. Similarly to the explanation in FIG. 4, the data processor 10 analyzes the signal detected by the one-dimensional sensors 11a and 11b and detects a peak position of the intensity distribution and an average position of the whole as a center position of the direct beam B2a.

When the X-ray beam B2 is reflected by the test face on the other hand, the beam reaches at the upper part of the one-dimensional sensors 11a and 11b and is detected as a reflected beam B2b. When a certain torsion angle exists due to the warp or deformation of the test product 20, the longitudinal direction of the reflected beam B2b is inclined and the detected positions of the reflected beam B2b differ from each other since the one-dimensional sensors 11a and 11b are set with the gap d. The data processor 10 analyzes the signal detected by the one-dimensional sensors 11a and 11b to detect a peak position of the intensity distribution or an average position of the whole as a center position of the reflected beam B2b and calculates a height H1 from the direct beam B2a to the reflected beam B2b in the one-dimensional sensor 11a and a height H2 from the direct beam B2a to the reflected beam B2b in the one-dimensional sensor 11b. Here, the center height H of the reflected beam B2b can be calculated as an average between H1 and H2 (=(H1+H2)/2) and an angle of inclination 2$\beta$ of the reflected beam B2b can be calculated as Arctan ((H2−H1)/2).

Next, similarly to the explanation in FIG. 4, it is possible to converge to the desirable X-ray irradiation condition by repeatedly controlling the position and angle of the test product 20 so that the condition of H=L×tan 2φ is satisfied and so that the angle of inclination of the intensity distribution of the reflected beam B2b is zeroed and so that the irradiation position of the X-ray beam B2 coincides with the desirable inspection point.

Figure 7:
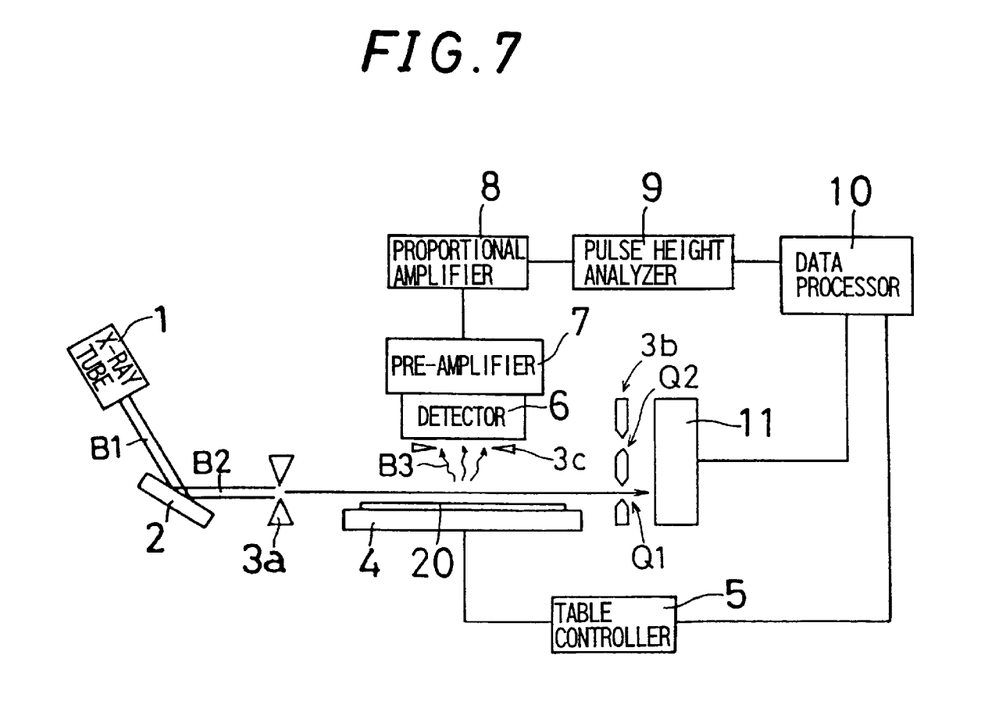
FIG. 7 is a structural diagram showing a third embodiment of the invention.

FIG. 7 is a structural diagram showing a third embodiment of the invention. While the X-ray analyzing apparatus shown in FIG. 7 has a similar structure with that shown in FIG. 1, it is different in that two openings Q1 and Q2 are created in the slit 3b and in that the slit controller 12 is omitted. It is noted that an explanation thereof which overlaps with the first embodiment will be omitted here to facilitate an understanding thereof.

The detector 11 detects the intensity of the X-ray beam B2 which has passed through the openings Q1 and Q2. Although a case in which one detector is used for the openings Q1 and Q2 is shown here, it is possible to provide two detectors for the openings Q1 and Q2, respectively.

FIGS. 8A through 8D are process diagrams showing an X-ray irradiation angle setting method according to the third embodiment.

At first, the test product 20 is set on the moving table 4 as shown in FIG. 7 and the height of the moving table 4 is controlled so that the X-ray beam B2 will not impinge on the test product 20. Here, a case in which the X-ray beam B2 travels in the horizontal direction (dashed line in FIG. 8) is shown. Next, the height of the slit 3b is controlled so that the x-ray beam B2 passes through the lower opening Q1 and the signal of the detector 11 is maximized. This position is defined as a reference height H0.

Figure 8A:
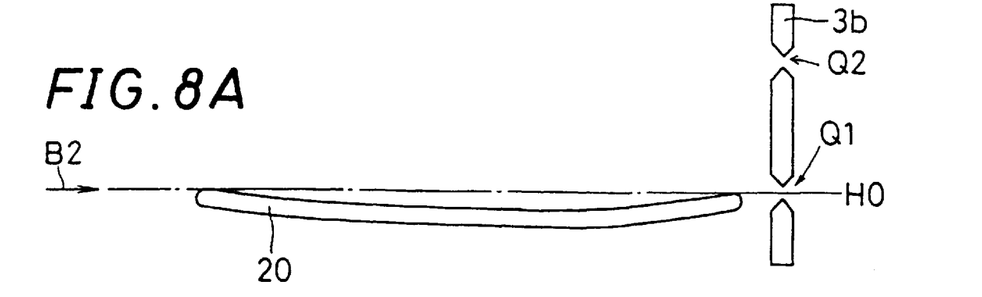
FIGS. 8A through 8D are process diagrams showing an X-ray irradiation angle setting method according to the third embodiment.

Next, the three-dimensional position and the angle of the test product 20 and the moving table 4 are controlled by detecting the change in intensity of the X-ray beam which is blocked by the test product 20 similarly to the procedure shown in FIG. 10 such that the traveling direction of the X-ray beam B2 becomes parallel with the face of the test product 20 as shown in FIG. 10E. Next, the change in intensity of the X-ray beam B2 which is blocked by the test product 20 is detected while moving the test product 20 in the direction almost perpendicular to the traveling direction of the X-ray beam B2 to set the test product 20 at a height where the test product 20 is on the verge of contacting the X-ray beam B2 as shown in FIG. 8A. It is noted that FIGS. 8A through 8D show a case when the test product 20 has a concaved deformation.

Figures 8B, 8C:
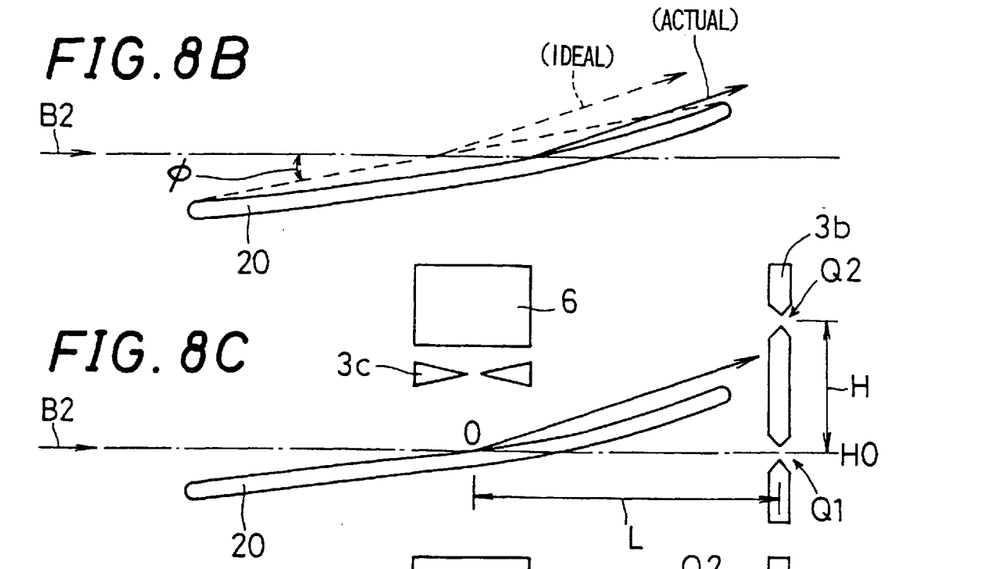

Next, the moving table 4 is inclined to set the incident angle to the X-ray beam B2 at a desirable angle φ as shown in FIG. 8B. This angle φ is a fully large angle which causes no blocked part due to the deformation, seeing the face of the test product 20 from the X-ray incident direction, and a very low angle which allows a full intensity of reflected X-rays to be maintained. It is preferable to be within a range of 0.05 to 0.3 degrees when the test product 20 is a silicon wafer for example.

If the face of the test product 20 is an ideal plane (indicated by a broken line in the FIG. 8B) in this state, the setting of the X-ray irradiation angle is finished. However, because the test product 20 has a deformation such as a warp more or less in general, the position where the X-ray beam B2 impinges on the test face is displaced in the horizontal direction and the X-ray incident angle is also shifted from the angle φ as shown in FIG. 8B.

Here, the upper opening Q2 is formed so as to define the pass position of the X-ray beam B2 reflected by the test face and the height H of the opening Q2 is set at L×tan 2φ, where L is a horizontal distance from the inspection point to the slit 3b and φ is an irradiation angle at the time of measurement. The position of the opening Q2 is the pass position of a regular reflection axis when the X-ray incident angle is the angle φ. It is noted that when the irradiation angle φ is small, it can be approximated by tan 2φ≈2φ.

Next, in order to make the irradiation position of the X-ray beam B2 coincident with the inspection point O, the detector 6 which is set almost right above the inspection point O detects scattered X-rays or fluorescent X-rays, other than the regular reflection, to control the height of the test product 20 so that the detected intensity is maximized. In this state, the X-ray irradiation position on the test face coincides with the inspection point O set on the light receiving center axis of the detector 6 as shown in FIG. 8C. The movement at this time is set as Δz.

Figure 8D:
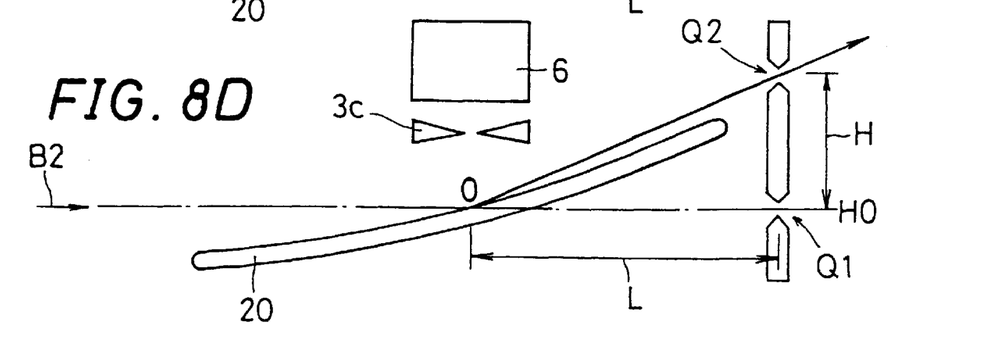

Because the X-ray incident angle is shifted from the angle φ due to the deformation of the test product 20 in the state shown in FIG. 8C, the axis of reflected X-rays can not pass through the opening Q2. Then, the test product 20 is angularly displaced centering on the inspection point O so that the reflected X-rays pass through the opening Q2 as shown in FIG. 8D and the angle of the test face is controlled so that the detected intensity at the detector 11 following the slit 3b is maximized. An angular displacement at this time is set as Δω.

Here, because the X-ray irradiation position may be shifted due to the angular control of the test product 20 when the deformation of the test product 20 is large, the height control using the detector 6 and the angular control using the detector 11 are repeated again several times so that the movement Δz and the angular displacement Δω converge below the specified values. It is noted that it is desirable to make the height and angle of the test product 20 to be set initially closer to the converged values as much as possible in order to converge such controls in a short time, and a measuring system using light may be provided separately.

Thus, the X-ray incident angle can be set at high precision and quickly even for a test product having a warp, by controlling the three-dimensional position and angle of the test product such that the detected intensities from the two detectors 6 and 11 are maximized.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. An X-ray analyzing apparatus for use in testing a product, said apparatus comprising:

an X-ray beam irradiating device operable to irradiate, at a predetermined angle, an X-ray beam to a test face of the product to be tested;

a slit member including a first opening for defining a first pass position of the X-ray beam, wherein the first pass position corresponds to a position of the X-ray beam after passing straight above the test face of the product, and a second opening for defining a second pass position of the X-ray beam, wherein the second pass position corresponds to a position of the X-ray beam after being reflected by the test face;

a first X-ray detector operable to detect an intensity of the X-ray beam which has passed through the first or second opening;

a product supporting device operable to support the product to control a three-dimensional position of the test face and an angle of the test face to the X-ray beam; and a second X-ray detector provided almost right above an inspection point, operable to detect an intensity of scattered X-rays or fluorescent X-rays from the test face.

2. An X-ray irradiation angle setting method for setting an irradiation angle of an X-ray beam to a test face of a product to be tested, comprising:

disposing a slit for defining a pass position of the X-ray beam reflected by the test face so as to set a height H of the slit to L×tan 2$\phi$, wherein L is a horizontal distance from an inspection point to the slit and $\phi$ is an irradiation angle at the time of measurement; and adjusting an angle of the product within a reflection plane so that the X-ray beam reflected by the test face passes through the slit.

3. An X-ray irradiation angle setting method for setting an irradiation angle of an X-ray beam to a test face of a product to be tested, comprising:

setting a height of the product by detecting a change in intensity of the X-ray beam blocked by the product while moving the product in a direction almost perpendicular to the traveling direction of the X-ray beam;

adjusting an angle of the product to the incident X-ray beam within a reflection plane so as to set the angle of the product at a predetermined irradiation angle;

disposing a slit for defining a pass position of the X-ray beam reflected by the test face and setting a height H of the slit to L×tan 2$\phi$, wherein L is a horizontal distance from an inspection point to the slit and $\phi$ is an irradiation angle at the time of measurement;

disposing an X-ray detector, for detecting scattered X-rays or fluorescent X-rays from the test face, almost right above the inspection point to adjust the height of the product so that a signal from the X-ray detector is maximized; and adjusting an angle of the product within the reflection plane so that the X-ray beam reflected by the test face passes through the slit.

4. An X-ray irradiation angle setting method for setting an irradiation angle of an X-ray beam to a test face of a product to be tested, comprising:

detecting an intensity distribution and a position of the X-ray beam which passed straight above the test face;

adjusting an angle of the product to the X-ray beam within a reflection plane so as to set the angle of the product at a predetermined incident angle;

detecting an intensity distribution and a position of the X-ray beam reflected by the test face; and adjusting a torsion angle of the product to the X-ray beam so that the intensity distribution of the reflected X-ray beam coincides with the intensity distribution of the X-ray beam which passed straight above the test face.

5. An X-ray irradiation angle setting method for setting an irradiation angle of an X-ray beam to a test face of a product to be tested, comprising:

disposing a slit member including a first opening for defining a pass position of the X-ray beam which has passed straight above the test face and a second opening for defining a pass position of the X-ray beam reflected by the test face and setting a height H of the second opening to L×tan 2$\phi$, wherein L is a horizontal distance from an inspection point to the slit and $\phi$ is an irradiation angle at the time of measurement; and adjusting an incident angle of the product within the reflection plane so that the X-ray beam reflected by the test face passes through the second opening.

* * * * *